(12) United States Patent
Govari et al.

(10) Patent No.: US 10,602,947 B2
(45) Date of Patent: Mar. 31, 2020

(54) HIGH DENSITY ELECTRODE STRUCTURE

(71) Applicant: BIOSENSE WEBSTER (ISRAEL), LTD., Yokneam (IL)

(72) Inventors: Assaf Govari, Haifa (IL); Christopher Thomas Beeckler, Brea, CA (US); Rowan Olund Hettel, Redondo Beach, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 814 days.

(21) Appl. No.: 13/860,921

(22) Filed: Apr. 11, 2013

(65) Prior Publication Data

US 2014/0309512 A1 Oct. 16, 2014

(51) Int. Cl.
| | |
|---|---|
| *A61B 5/042* | (2006.01) |
| *A61B 18/14* | (2006.01) |
| *A61N 1/05* | (2006.01) |
| *A61M 25/16* | (2006.01) |
| *A61B 5/00* | (2006.01) |

(Continued)

(52) U.S. Cl.
CPC .......... *A61B 5/0422* (2013.01); *A61B 5/6858* (2013.01); *A61B 18/1492* (2013.01); *A61N 1/05* (2013.01); *A61N 1/056* (2013.01); *G02B 6/04* (2013.01); *G02B 6/449* (2013.01); *H01B 7/009* (2013.01); *H01B 13/0036* (2013.01); *H01B 13/06* (2013.01); *A61B 2017/00526* (2013.01); *A61B 2018/0016* (2013.01); *A61B 2018/00178* (2013.01); *A61B 2018/00267* (2013.01); *A61B 2562/125* (2013.01); *A61B 2562/222* (2013.01); *Y10T 29/49169* (2015.01); *Y10T 29/49174* (2015.01); *Y10T 29/49801* (2015.01)

(58) Field of Classification Search
CPC .... A61B 18/1492; A61B 5/6858; A61N 1/05; A61N 1/056; A61N 1/048; A61N 1/0488; A61N 1/086; H01B 7/009; A61M 25/0009; A61M 25/0012; A61M 25/0015; A61M 25/0662; A61M 25/09
USPC .......................................... 600/373
See application file for complete search history.

(56) References Cited

U.S. PATENT DOCUMENTS

| | | |
|---|---|---|
| 4,280,511 A | 7/1981 | O'Neill |
| 4,437,474 A | 3/1984 | Peers-Trevarton |
| (Continued) | | |

FOREIGN PATENT DOCUMENTS

| | | |
|---|---|---|
| CN | 101888812 | 11/2010 |
| EP | 0 617 916 A1 | 10/1994 |
| (Continued) | | |

OTHER PUBLICATIONS

European Search Report completed Mar. 4, 2015 for corresponding Application No. EP14190334.

(Continued)

*Primary Examiner* — Lee S Cohen
*Assistant Examiner* — Erin M Cardinal
(74) *Attorney, Agent, or Firm* — Dergosits & Noah LLP; Todd A. Noah (57) ABSTRACT

Electrode cabling, including a core and n wires coiled on the core in an arrangement topologically equivalent to an n-start thread configuration, wherein n is an integer greater than one. The cabling also includes a sheath covering the n wires and an electrode attached through the sheath to a given wire selected from the n wires.

37 Claims, 8 Drawing Sheets

(51) Int. Cl.
*H01B 7/00* (2006.01)
*H01B 13/06* (2006.01)
*G02B 6/04* (2006.01)
*G02B 6/44* (2006.01)
*H01B 13/00* (2006.01)
*A61B 18/00* (2006.01)
*A61B 17/00* (2006.01)

(56) References Cited

U.S. PATENT DOCUMENTS

| | | | | |
|---|---|---|---|---|
| 4,630,611 | A * | 12/1986 | King | A61B 5/0488 600/377 |
| 5,016,646 | A * | 5/1991 | Gotthardt | A61N 1/056 607/122 |
| 5,391,199 | A | 2/1995 | Ben-Haim | |
| 5,439,485 | A * | 8/1995 | Mar | A61N 1/0563 607/119 |
| 5,476,495 | A * | 12/1995 | Kordis | A61B 5/0422 600/374 |
| 5,555,618 | A * | 9/1996 | Winkler | A61B 5/0422 29/825 |
| 5,591,142 | A * | 1/1997 | Van Erp | A61B 5/6852 604/264 |
| 5,755,687 | A * | 5/1998 | Donlon | A61B 17/12022 600/18 |
| 5,772,590 | A | 6/1998 | Webster, Jr. | |
| 5,796,044 | A * | 8/1998 | Cobian | A61N 1/056 174/103 |
| 5,836,946 | A | 11/1998 | Diaz | |
| 5,911,739 | A | 6/1999 | Kordis et al. | |
| 6,004,269 | A * | 12/1999 | Crowley | A61B 8/4461 600/374 |
| 6,064,905 | A | 5/2000 | Webster, Jr. et al. | |
| 6,213,995 | B1 | 4/2001 | Steen et al. | |
| 6,239,724 | B1 | 5/2001 | Doron et al. | |
| 6,289,250 | B1 * | 9/2001 | Tsuboi | A61N 1/05 600/374 |
| 6,332,089 | B1 | 12/2001 | Acker et al. | |
| 6,400,981 | B1 | 6/2002 | Govari | |
| 6,484,118 | B1 | 11/2002 | Govari | |
| 6,584,345 | B2 | 6/2003 | Govari | |
| 6,618,612 | B1 | 9/2003 | Acker et al. | |
| 6,690,963 | B2 | 2/2004 | Ben-Haim et al. | |
| 6,748,255 | B2 | 6/2004 | Fuimaono et al. | |
| 6,973,340 | B2 | 12/2005 | Fuimaono et al. | |
| 7,149,585 | B2 * | 12/2006 | Wessman | A61N 1/05 219/522 |
| 7,229,437 | B2 | 6/2007 | Johnson | |
| 7,239,922 | B1 | 7/2007 | Boogaard et al. | |
| 2002/0022782 | A1 | 2/2002 | Kiepen et al. | |
| 2002/0038139 | A1 * | 3/2002 | Wessman | A61N 1/05 607/122 |
| 2002/0065455 | A1 | 5/2002 | Ben-Haim et al. | |
| 2002/0143377 | A1 * | 10/2002 | Wessman | A61N 1/05 607/116 |
| 2003/0092303 | A1 * | 5/2003 | Osypka | A61N 1/056 439/274 |
| 2003/0120150 | A1 | 6/2003 | Govari | |
| 2004/0059404 | A1 | 3/2004 | Bjorklund | |
| 2004/0068178 | A1 | 4/2004 | Govari | |
| 2006/0009404 | A1 * | 1/2006 | Williams | A61B 18/1477 514/44 R |
| 2010/0211147 | A1 * | 8/2010 | Schiefer | A61N 1/05 607/116 |
| 2011/0137382 | A1 * | 6/2011 | Swanson | A61N 1/0553 607/72 |
| 2012/0172714 | A1 | 7/2012 | Govari | |
| 2012/0172717 | A1 * | 7/2012 | Gonda | A61B 5/042 600/424 |
| 2012/0271135 | A1 * | 10/2012 | Burke | A61B 5/0422 600/373 |
| 2012/0271385 | A1 | 10/2012 | Li et al. | |
| 2012/0323089 | A1 | 12/2012 | Feer et al. | |
| 2013/0150808 | A1 * | 6/2013 | Ogle | A61M 25/0012 604/264 |
| 2013/0197616 | A1 * | 8/2013 | Dollimer | A61N 1/05 607/116 |
| 2014/0309512 | A1 | 10/2014 | Govari et al. | |
| 2016/0183877 | A1 | 6/2016 | Williams et al. | |

FOREIGN PATENT DOCUMENTS

| | | |
|---|---|---|
| EP | 1723981 A1 | 11/2006 |
| EP | 2471480 A1 | 7/2012 |
| JP | S57128805 U | 8/1982 |
| JP | H08511438 | 12/1996 |
| JP | H10510731 | 10/1998 |
| JP | 2004130114 | 4/2004 |
| JP | 2010057943 | 3/2010 |
| JP | 2012510831 | 5/2012 |
| WO | 96/05768 A1 | 2/1996 |
| WO | WO 00/0062851 A1 | 10/2000 |
| WO | WO 2009/072039 A2 | 6/2009 |
| WO | WO 2009/085486 A1 | 7/2009 |

OTHER PUBLICATIONS

EP Search Report 14 16 2843.8-1659 dated Aug. 11, 2014.
U.S. Appl. No. 14/063,477, filed Oct. 25, 2013.
U.S. Appl. No. 14/824,508, filed Aug. 12, 2015.
European Search Report dated Jan. 12, 2017 for corresponding EP 16183699.4.
Office Action for U.S. Appl. No. 14/063,477, dated Jun. 27, 2017.
Office Action for U.S. Appl. No. 14/063,477, dated Mar. 21, 2017.
Office Action for U.S. Appl. No. 14/063,477, dated Oct. 4, 2016.
Office Action for China Patent Application No. 20144233.9, dated Oct. 25, 2017.
Examination Report for Australia Patent Application No. 2014201935, dated Jun. 14, 2017.
Office Action for U.S. Appl. No. 14/063,477, dated Jan. 4, 2018.
Office Action for U.S. Appl. No. 14/063,477, dated Apr. 18, 2018.
Office Action for U.S. Appl. No. 14/824,508, dated Apr. 18, 2018.
Examination Report for Australia Patent Application No. 2014201935, dated Feb. 21, 2018.
Examination Report for Europe Patent Application No. 14190334.4, dated Feb. 28, 2018.
Notification for Reasons of Refusal for Japan Patent Application No. 2014-080835, dated Jan. 30, 2018.
Examination Report for Australia Patent Application No. 2014248091, dated Jun. 26, 2018.
Office Action for China Patent Application No. 20144233.9, dated Jun. 11, 2018.
Examination Report for European Patent Application No. 14162843.8, dated May 14, 2018.
Examination Report for European Patent Application No. 16183699.4, dated Jun. 8, 2018.
Notification for Reasons of Refusal for Japan Patent Application No. 2014-080835, dated Jun. 26, 2018.
Notification for Reasons of Refusal for Japan Patent Application No. 2014-217009, dated Aug. 7, 2018.

* cited by examiner

FIG. 7

HIGH DENSITY ELECTRODE STRUCTURE

FIELD OF THE INVENTION

The present invention relates generally to cabling, and specifically to cabling having conductors built into the cabling.

BACKGROUND OF THE INVENTION

A medical catheter, when used invasively on a patient, is an example of a probe where the outside diameter of the catheter is a critical measurement. In general, the smaller the diameter of the catheter, the better. On the other hand, the catheter is normally used to deliver entities, such as sensors or electrodes, to an internal organ of the patient, and these entities, and their associated wiring, may limit the extent to which the catheter diameter may be reduced.

A system which enables reduction in the diameter of a catheter, while allowing large numbers of entities such as sensors or electrodes to be incorporated into the catheter, would thus be advantageous.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides electrode cabling, including:

a core;

n wires coiled on the core in an arrangement topologically equivalent to an n-start thread configuration, wherein n is an integer greater than one;

a sheath covering the n wires; and an electrode attached through the sheath to a given wire selected from the n wires.

Typically the n wires include n respective conductors having n respective insulating layers.

In a disclosed embodiment the cabling includes up to (n−1) further electrodes attached through the sheath to up to (n−1) respective wires other than the given wire.

In a further disclosed embodiment at least one of the n wires is configured to act as an index wire for the n wires. Typically, the index wire is visually different in appearance from the n wires not including the index wire.

Typically, the sheath is transparent.

The electrode may be attached to the given wire at a distal end of the cabling, and the cabling may include a connector attached at a proximal end of the cabling to the given wire.

The cabling may be configured for use as a medical catheter.

In a yet further disclosed embodiment the core is cylindrical, and the n wires are coiled on the core in the n-start thread configuration.

Typically, the core encloses a shape element.

In an alternative embodiment the cabling includes n filaments coiled on the core and configured to respectively separate the n wires.

In a further alternative embodiment the cabling has n spaces configured to respectively separate the n wires.

There is further provided, according to an embodiment of the present invention, a catheter, including:

a retaining cable, including a plurality of electrode cablings, each electrode cabling including:

a core;

n wires coiled on the core in an arrangement topologically equivalent to an n-start thread configuration, wherein n is an integer greater than one;

a sheath covering the n wires; and up to n electrodes respectively attached through the sheath to up to n different wires of the arrangement.

In a disclosed embodiment the distal ends of the plurality of electrode cablings are configured as spokes radiating from the retaining cable. Typically, the spokes form a plane orthogonal to the retaining cable. Alternatively, the spokes form a plane which includes the retaining cable.

In a further disclosed embodiment distal ends of the plurality of electrode cablings are configured as spines of a basket assembly, wherein the spines are connected at the proximal ends thereof to the retaining cable, and are connected at the distal ends thereof. Typically, the spines are equal in length. Alternatively, the spines are unequal in length. The spines may form ribs of a hemisphere.

There is further provided, according to an embodiment of the present invention, a method, including:

coiling n wires on a core in an arrangement topologically equivalent to an n-start thread configuration, wherein n is an integer greater than one;

covering the n wires with a sheath; and attaching an electrode through the sheath to a given wire in the arrangement.

There is further provided, according to an embodiment of the present invention, a method for producing a catheter, including:

enclosing a plurality of electrode cablings within a retaining cable; and for each electrode cabling:

coiling n wires on a core in an arrangement topologically equivalent to an n-start thread configuration, wherein n is an integer greater than one;

covering the n wires with a sheath; and respectively attaching up to n electrodes through the sheath to up to n different wires in the arrangement.

There is further provided, according to an embodiment of the present invention, cabling, including:

a core;

n optical fibers coiled on the core in an arrangement topologically equivalent to an n-start thread configuration, wherein n is an integer greater than one; and a sheath covering the n optical fibers.

The cabling may include a sensor attached through the sheath to a given fiber selected from the optical fibers.

There is further provided, according to an embodiment of the present invention, cabling, including:

a core;

n optical fibers coiled on the core, wherein n is an integer greater than zero;

m wires coiled on the core, wherein m is an integer greater than zero, and wherein the n optical fibers and the m wires are coiled on the core in an arrangement topologically equivalent to an (n+m)-start thread configuration; and a sheath covering the n optical fibers and the m wires.

There is further provided, according to an embodiment of the present invention, a method, including:

coiling n optical fibers on a core in an arrangement topologically equivalent to an n-start thread configuration, wherein n is an integer greater than one; and covering the n optical fibers with a sheath.

There is further provided, according to an embodiment of the present invention, a method, including:

coiling n optical fibers on a core, wherein n is an integer greater than zero;

coiling m wires coiled on the core, wherein m is an integer greater than zero, and wherein the n optical fibers and the m wires are coiled on the core in an arrangement topologically equivalent to an (n+m)-start thread configuration; and covering the n optical fibers and the m wires with a sheath.

The present disclosure will be more fully understood from the following detailed description of the embodiments thereof, taken together with the drawings, in which:

DETAILED DESCRIPTION OF EMBODIMENTS

Overview

An embodiment of the present invention provides cabling to which a high density of electrodes may be attached, the cabling and electrodes typically being used as part of a medical catheter. The cabling comprises insulated wires which are coiled around a core in an arrangement that is topologically equivalent to a multi-start thread configuration. Thus, assuming there are n wires, where n is an integer greater than one, the n wires are coiled in an arrangement topologically equivalent to an n-start thread configuration.

A sheath covers the n wires, and up to n electrodes may be attached through the sheath to different respective wires.

Typically the core is a plastic cylindrical tube, in which case the n wires may be coiled on the core in the n-start thread configuration.

Forming cabling by coiling n wires around a core, in the arrangement described above, permits the diameter of the cabling to be minimized. While the diameter is minimal, the arrangement allows a high density of electrodes, or other objects requiring connection to conductors in the wires, to be attached to the cabling.

In some embodiments, at least some of the wires are replaced by optical fibers, the optical fibers and/or the wires operating as active elements capable of transferring signals. The active elements may be separated by inactive filaments which do not transfer signals.

System Description

Figure 1A:
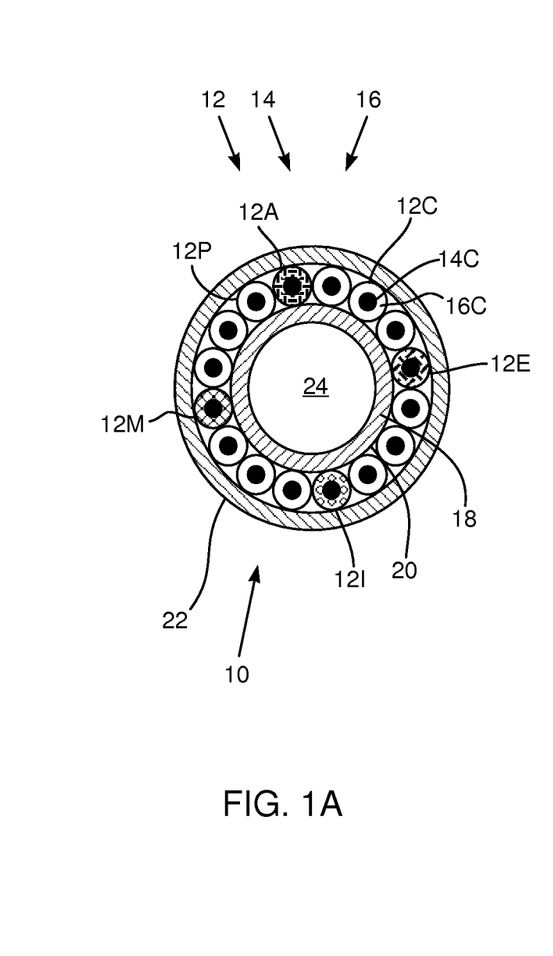
FIGS. 1A and 1B are respectively schematic cross-sectional and side views of a central section of cabling, according to an embodiment of the present invention.
Figure 1B:
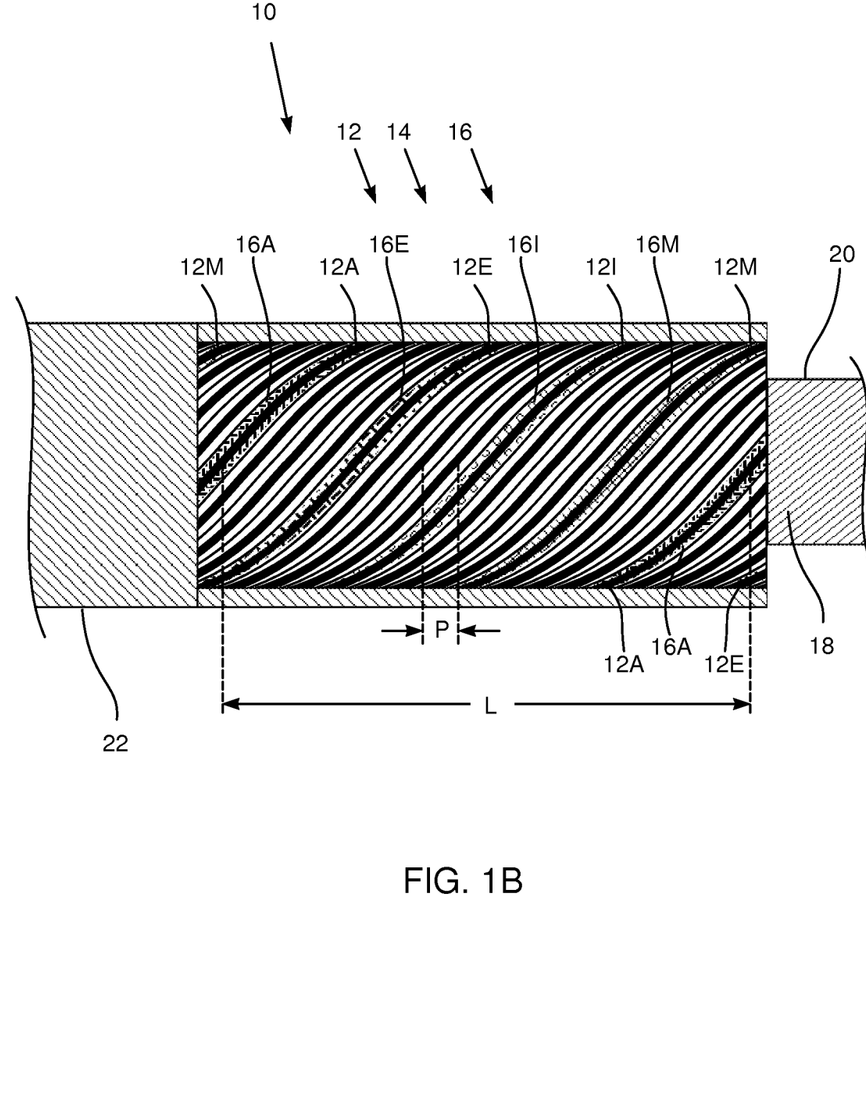

Reference is now made to FIGS. 1A and 1B, which are schematic views of cabling 10, according to an embodiment of the present invention. FIG. 1A is a schematic cross-sectional view of the cabling. FIG. 1B is a schematic, side view of cabling 10, which has been partially cut-away to expose internal elements of the cabling. As is explained further below, electrodes may be attached to the cabling, and the cabling is configured so that a large number of separate electrodes, each having respective attached wires, may be attached in a small length of the cabling, so that cabling 10 is capable of supporting a high density of electrodes. Cabling 10 is typically used as part of a medical catheter wherein electrical measurements are to be made from the electrodes attached to the cabling.

Cabling 10 comprises a plurality of generally similar wires 12, each wire 12 being formed as a conductor 14 covered by an insulating layer 16. In the following description, generally similar components associated with cabling 10 are referred to generically by their identifying component numeral, and are differentiated from each other, as necessary, by appending a letter A, B, . . . to the numeral. Thus wire 12C is formed as conductor 14C covered by insulating layer 16C. While embodiments of the present invention may be implemented with substantially any plurality of wires 12 in the cabling, for clarity and simplicity in the following description cabling 10 is assumed to comprise 16 wires 12A, . . . 12E, . . . 12I, . . . 12M, . . . 12P.

(For purposes of illustration, insulating layers 16 of wires 12 have been drawn as having approximately the same dimensions as conductors 14. In practice, the insulating layer is typically approximately one-tenth the diameter of the wire.)

In order to be used as part of a medical catheter, an outer diameter of cabling 10 is implemented to be as small as possible. In one embodiment, cabling 10 is approximately cylindrical with a length of approximately 2 m, and an outer diameter approximately equal to 0.5 mm. Because of the small outer diameter of cabling 10 catheters may be implemented using two or more sets of the cabling, as well as just one set of the cabling. Examples of catheters using multiple sets of cabling 10 are provided below.

Wires 12 may be formed with any diameter wire that is consistent with the outer diameter of cabling 10. In one embodiment wires 12 are formed of 48 AWG wire, corresponding to a wire diameter of approximately 30 microns. In some embodiments of the present invention the inventors have used, inter alia, monel, constantan, or copper for conductors 14. While copper has a higher electrical conductivity than monel or constantan, it may have a tendency to break during production (described below) of the cabling. Both monel and constantan enhance the strength of cabling 10, but in environments where magnetic properties of materials are significant, such as during a magnetic resonance imaging procedure or in a catheter using magnetic navigation, it may be preferable to use constantan for conductors 14. While monel, constantan and copper are provided as examples of the material used for conductors 14, it will be understood that embodiments of the present invention are not limited to a particular type of material, and any other convenient electrically conducting material may be used. In some embodiments wires that neighbor each other may be selected to have dissimilar conductors, such as copper and constantan, so as to be available for forming a thermocouple junction.

Wires 12 are formed over an internal core 18, which is typically shaped as a cylindrical tube, and core 18 is also referred to herein as tube 18. The core material is typically selected to be a thermoplastic elastomer such as a polyether block amide (PEBA). In a disclosed embodiment core 18 is formed of 40D Pebax, produced by Arkema, Colombes, France. In the disclosed embodiment core 18, by way of example, is cylindrical with a wall thickness of approximately 13 microns, and an outer diameter of approximately 0.4 mm. Wires 12 are formed on an outer surface 20 of core 18 by coiling the wires around the tube. Thus, in the case that core 18 is cylindrical, each wire 12 on the outer surface is in the form of a helical coil. In contrast to a braid, all helical coils of wires 12 have the same handedness.

In coiling wires 12 on surface 20, the wires are arranged so that they contact each other in a "close-packed" configuration. In other words, if internal tube 18 were to be opened so that surface 20 is a flat plane, the wires (neglecting "end-effects") form a single wire layer over surface 20, with insulating layers 16 continuously in contact with two other insulating layers, and with the insulating layers being continuously in contact with surface 20.

In the case of tube 18 being cylindrical, the close-packed arrangement of the helical coils of wires 12 means that the wires are configured in a multi-start thread configuration. Thus, in the case of the 16 wires 12 assumed herein, wires 12 are arranged in a 16-start thread configuration around cylindrical tube 18. For the 16-start configuration, a relationship between distances of wires 12 in the configuration is given by equation (1):

$$L = 16 \cdot P \quad (1)$$

where P is the distance between adjacent wires of the configuration, and

L is the length along tube 18 between corresponding sections of the same wire 12.

In FIG. 1B sheath 22 of cabling 10 has been cut-away to illustrate length L and distance P.

In general, for n wires 12, where n is an integer greater than one, the n wires are arranged in an n-start thread configuration, and equation (2) holds:

$$L = n \cdot P \quad (2)$$

Where L, n, and P are as defined above.

It will be appreciated that equation (2) corresponds to the equation for a multi-start thread relating the pitch, the lead, and the number of starts of the thread.

The arrangement of wires in embodiments of the present invention contrasts with arrangements of wires in braids around a cylinder. Wires in braids surrounding a cylinder are interleaved, so are not in the form of helices. Because of the non-helical nature of the wires in braids, even braid wires with the same handedness do not have a thread form, let alone a multi-start thread configuration. Furthermore, because of the lack of interleaving in arrangements of wires in embodiments of the present invention, the overall diameter of the cabling produced is less than that of cabling using a braid, and the reduced diameter is particularly beneficial when the cabling is used for a catheter.

Although, as described in more detail below, cabling 10 may be assembled while tube 18 has a cylindrical form, there may be cases where the cylindrical form is deformed. Such a case occurs where tube 18 is flattened, so that instead of having a circular cross-section due to its cylindrical form, the tube has an oval or elliptical cross-section. In these cases, while the arrangement of wires 12 is no longer a multi-start thread configuration, because the wires have been deformed from a helical shape, the arrangement of wires 12 around deformed tube 18 is topologically equivalent to a multi-start thread configuration. I.e., the wires have the same close-packed characteristics described above, the wires form a single wire layer over surface 20 of tube 18, have insulating layers continuously in contact with two other insulating layers, and the insulating layers are continuously in contact with the surface of the tube. Furthermore, equation (2) holds. It will also be appreciated that in all cases wires 12 are congruent to each other, and from a geometrical point of view any given wire 12 may be transformed to another wire by a translation parallel to an axis of tube 18.

For simplicity, in the description hereinbelow, tube 18 is assumed to be cylindrical.

Once wires 12 have been formed in the multi-start thread configuration described above, the wires are covered with a protective sheath 22. The protective sheath material is typically selected to be a thermoplastic elastomer such as PEBA. In a disclosed embodiment sheath 22 is formed of 55D Pebax, produced by Arkema, and no additives are incorporated in the sheath, so that it is transparent. In the disclosed embodiment sheath 22, by way of example, has an outer diameter of approximately 0.5 mm.

Typically, although not necessarily, the insulating layer of at least one of wires 12 is colored differently from the colors of the remaining wires. Such coloration aids in identifying particular wires once they have been arranged within cabling 10, assuming that sheath 22 is transparent. An alternative method for identifying particular wires in a braided arrangement is described in U.S. Patent Application 2012/0172714 to Govari et al., which is incorporated herein by reference. The method described therein may be used, mutatis mutandis, to identify wires in embodiments of the present invention, regardless of whether sheath 22 is configured to be transparent.

By way of example, in the embodiment using 16 wires every fourth wire has its insulating layer colored, so that insulating layers 16A, 16E, 16I, and 16M are respectively colored green, black, red, and violet. The insulating layers of the remaining wires may be given another color, such as white, or may be left colorless. Thus, wires 12A, 12E, 12I, and 12M appear to have the colors green, black, red, and violet, and are visually different in appearance from the remaining wires.

The process of coiling wires 12 around a core, and then covering the wires by a sheath, essentially embeds the wires within a wall of cabling 10, the wall consisting of the core and the sheath. Embedding the wires within a wall means that the wires are not subject to mechanical damage when the cabling is used to form a catheter. Mechanical damage is prevalent for small wires, such as the 48 AWG wires exemplified above, if the wires are left loose during assembly of a catheter.

Furthermore, in use as a catheter, an approximately cylindrical volume 24 enclosed by core 18, that is afforded by embedding smaller wires (such as the 48 AWG wires) in the wall, allows at least a portion of the cylindrical volume to be used for a stiffening or shape element (like Nitinol). This enables differently-shaped catheters to be constructed.

Figure 2A:
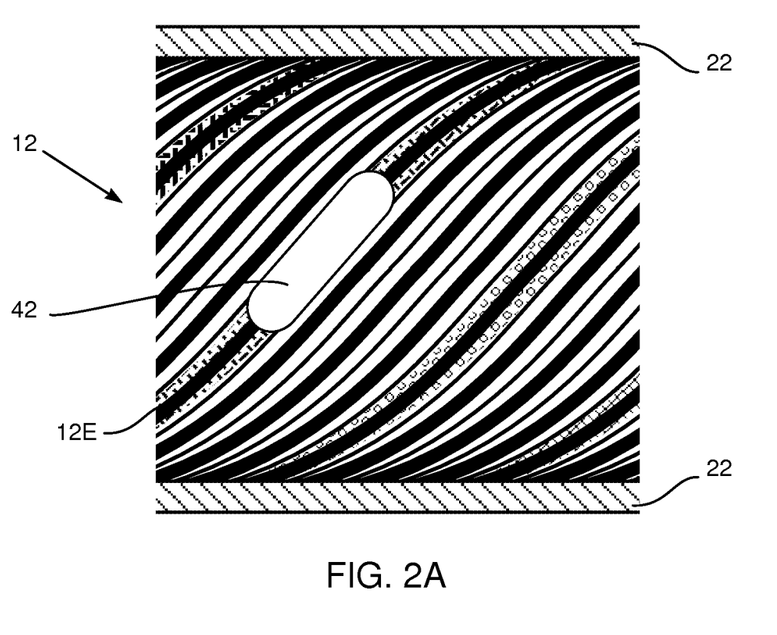
FIGS. 2A and 2B are schematic diagrams illustrating attachment of an electrode to the cabling, according to an embodiment of the present invention.
Figure 2B:
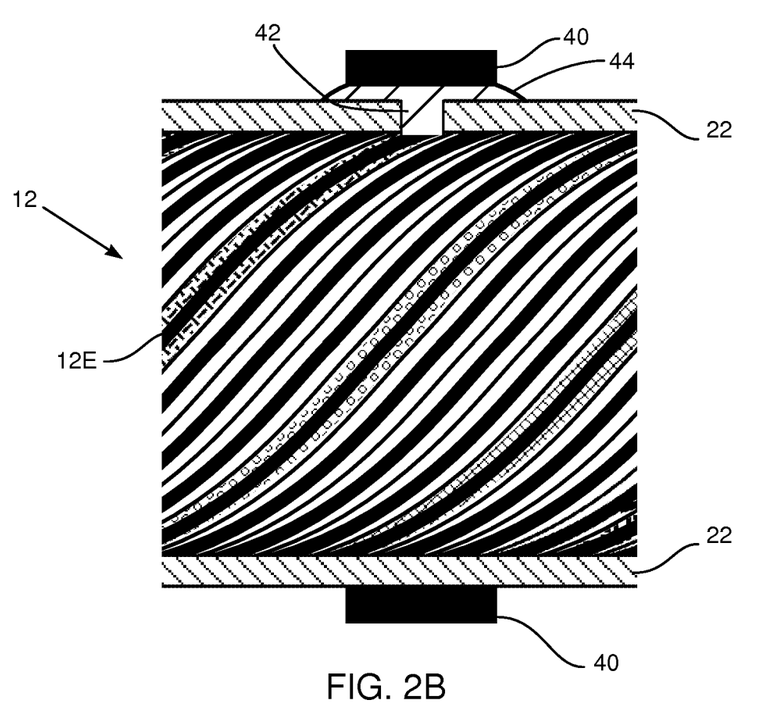

FIGS. 2A and 2B are schematic diagrams illustrating attachment of an electrode to cabling 10, according to an embodiment of the present invention. FIG. 2A is a schematic top view of the cabling and FIG. 2B is a schematic side view of the cabling; in both views parts of sheath 22 have been cut-away to expose wires 12 of cabling 10, as well as to illustrate the attachment of an electrode 40 to the cabling. FIG. 2A illustrates cabling 10 before attachment of electrode 40, and FIG. 2B illustrates the cabling after the electrode has been attached.

Electrode 40 is typically in the form of a conductive ring with dimensions enabling it to be slid over sheath 22. The following explanation assumes that the electrode is to be attached to colored wire 12E at a distal end of cabling 10.

Initially a location for attaching the electrode is selected by finding colored wire 12E visually. The visual determination is possible since sheath 22 is transparent. Once the location has been selected, a section of sheath above the wire, and a corresponding section of insulating layer 16E, are removed, to provide a channel 42 to conductor 14E.

In a disclosed embodiment conductive cement 44 is fed into the channel, electrode 40 is slid to contact the cement, and the electrode is then crimped in place. Alternatively, electrode 40 may be attached to a specific wire by pulling the wire through sheath 22, and resistance welding or soldering the electrode to the wire. Further details of the attachment of electrodes to cabling 10 are provided below.

Figure 3A:
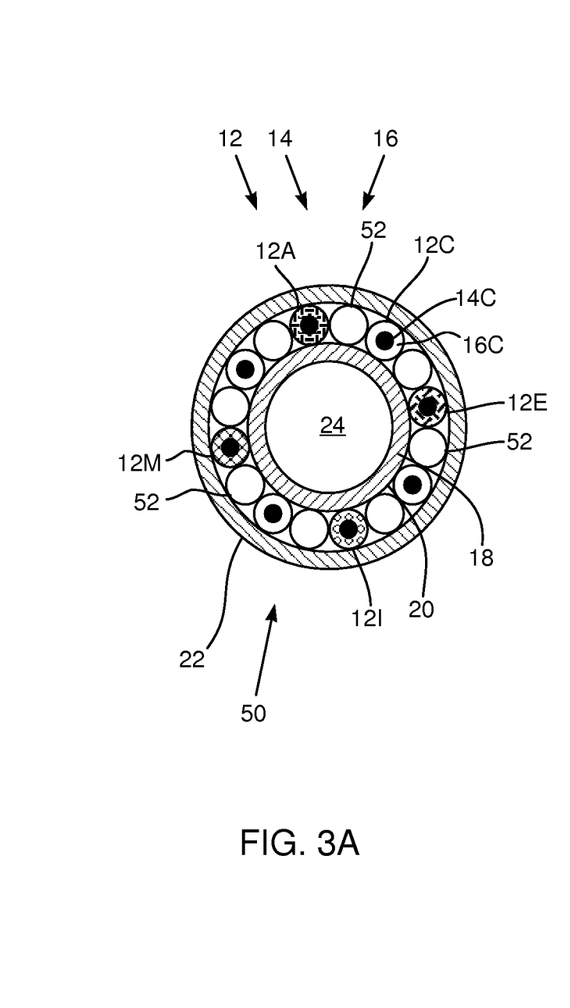
FIGS. 3A and 3B are schematic views of cabling, according to an alternative embodiment of the present invention.
Figure 3B:
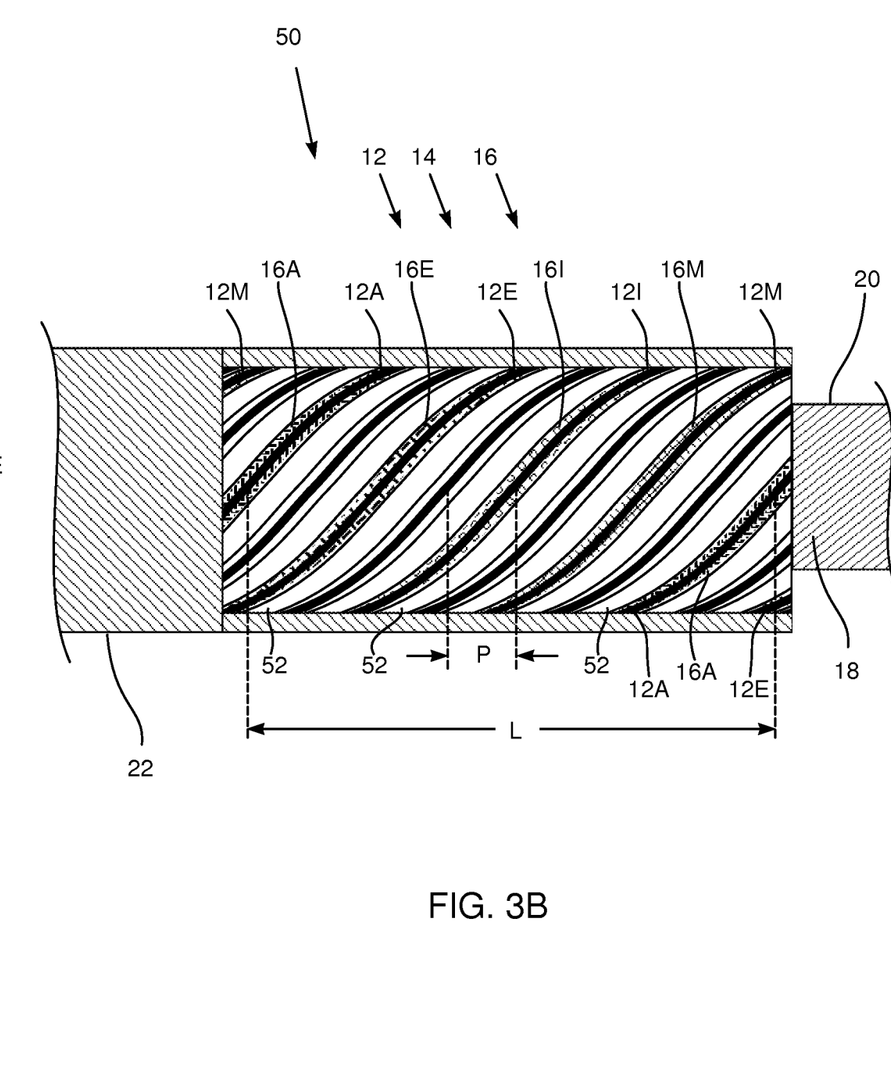

FIGS. 3A and 3B are schematic views of cabling 50, according to an embodiment of the present invention. FIG. 3A is a schematic cross-sectional view of cabling 50. FIG. 3B is a schematic, side view of cabling 50, which has been partially cut-away to expose internal elements of the cabling. Apart from the differences described below, the structure of cabling 50 is generally similar to that of cabling 10 (FIGS. 1A and 1B), and elements indicated by the same reference numerals in both cabling 50 and 10 are generally similar in construction and in operation.

In contrast to cabling 10, where wires 12 are in contact with each other, in cabling 50 wires 12 are separated from each other by an equal number of non-signal conducting filaments 52, filaments 52 typically having the same outer diameter as wires 12. The figures illustrate an example of cabling 50 having eight wires 12 separated by eight filaments 52, but the number of wires and filaments may be larger or smaller than eight. In a disclosed embodiment cabling 50 comprises 16 wires separated from each other by 16 filaments.

In one embodiment filaments 52 are formed of PEN (polyethylene naphthalate). The combination of wires 12 with filaments 52 in cabling 50 has a similar close-packed structure as that described above for cabling 10. Thus, for example, from a geometrical point of view any given wire 12 or filament 52 may be transformed to another wire or filament by a translation parallel to an axis of tube 18.

Cabling 50 has a similar multi-start thread configuration to that of cabling 10, and the figures illustrate cabling 50 in an 8-start thread configuration. As for cabling 10, equation (2) holds for cabling 50, where L, P, and n are as defined above. As illustrated in FIG. 3B P is the distance between adjacent wires, which are now separated by one filament 52.

While the configuration of cabling 50 reduces the density of electrodes that may be attached to the cabling, compared to that of cabling 10, the inventors have found that the addition of filaments 52 increases the flexibility of the cabling. The configuration of cabling 50 also makes exposure of a specific wire 12 easier, by reducing the chance of inadvertently exposing a neighboring wire.

Figure 4A:
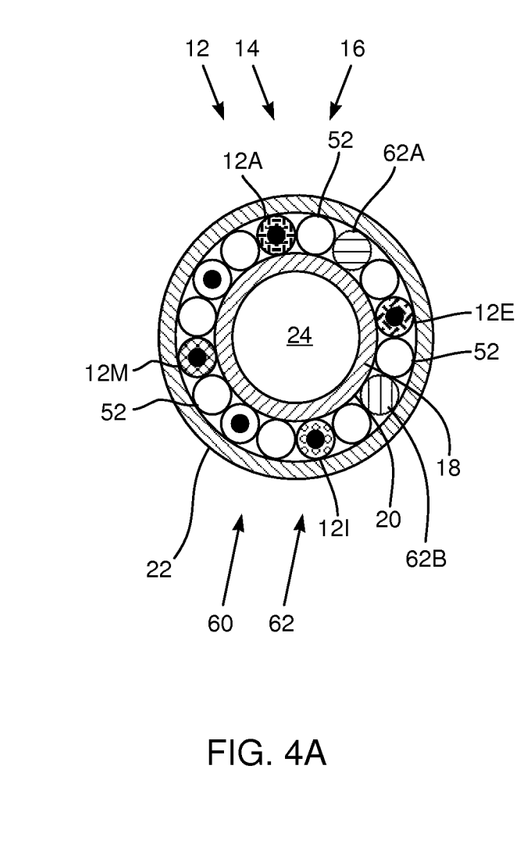
FIGS. 4A and 4B are schematic views of cabling, according to a further alternative embodiment of the present invention.
Figure 4B:
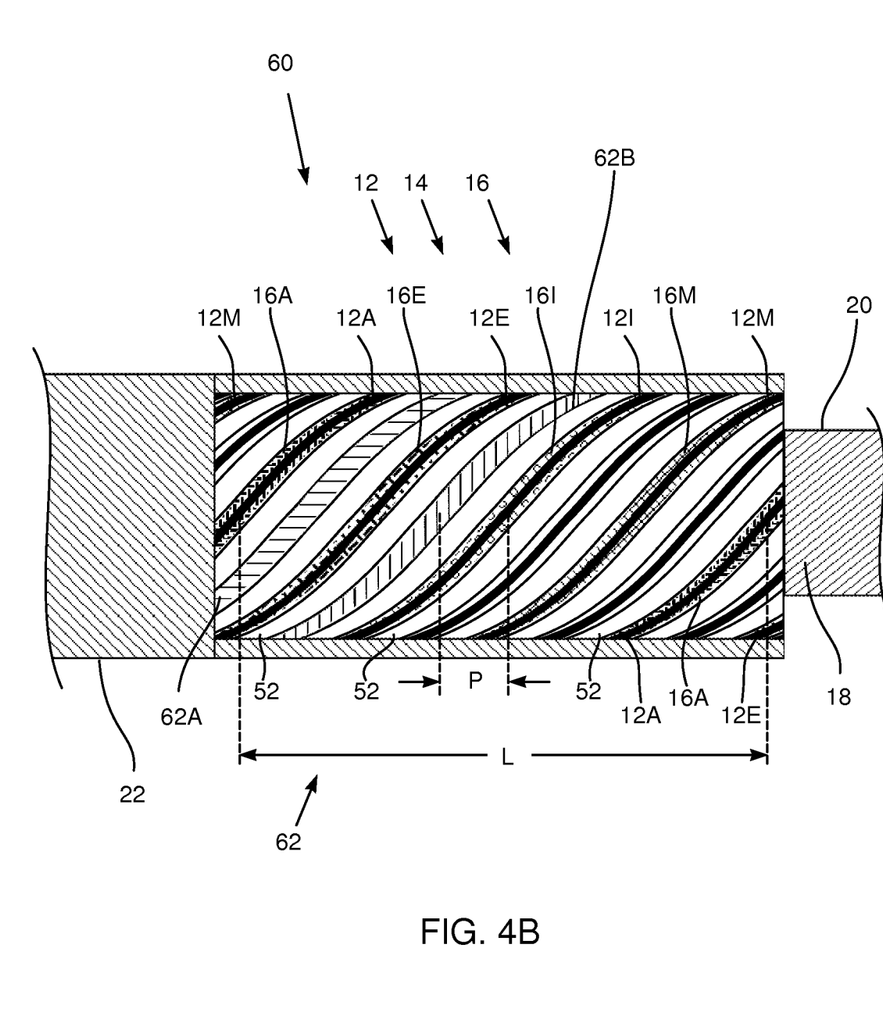

FIGS. 4A and 4B are schematic views of cabling 60, according to an embodiment of the present invention. FIG. 4A is a schematic cross-sectional view of cabling 60. FIG. 4B is a schematic, side view of cabling 60, which has been partially cut-away to expose internal elements of the cabling. Apart from the differences described below, the structure of cabling 60 is generally similar to that of cabling 50 (FIGS. 3A and 3B), and elements indicated by the same reference numerals in both cabling 50 and 60 are generally similar in construction and in operation.

In contrast to cabling 50, and to cabling 10, where all active elements comprise wires 12 having respective electrical conductors, in cabling 60 at least one active element comprises an optical fiber. An active element is assumed herein to comprise an entity that is able to convey electrical or electromagnetic signals. By way of example, cabling 60 is assumed to comprise an optical fiber 62A, and an optical fiber 62B, which replace respective wires 12 in cabling 50. The optical fibers, referred to herein generically as fibers 62, may be used to transmit light to, or collect light from, the distal end of cabling 60.

Typically, the light travelling in fibers 62 may be configured to convey information between the distal and proximal ends of the cabling, for example by amplitude or wavelength modulation of the light. Alternatively or additionally, at least one fiber 62 may be terminated by a corresponding sensor; for example, a diffraction grating for use as a force sensor may be connected to or incorporated into fiber 62A at the distal end of the fiber.

Cabling 60 has a mixture of active elements, and is illustrated as having six wires 12 and two optical fibers 62, for a total of eight active elements. In general, cabling 60 may comprise n wires 12 and m optical fibers 62, where m,n are integers greater than zero. In the general case the n wires and the m optical fibers are coiled around core 18 in an arrangement that is topologically equivalent to an (n+m)-start thread configuration.

While cabling 60, in the examples described above, comprises a mixture of active elements, i.e., wires 12 and optical fibers 62, in some embodiments of the present invention the active elements of cabling 60 comprise only optical fibers 62.

Figure 5:
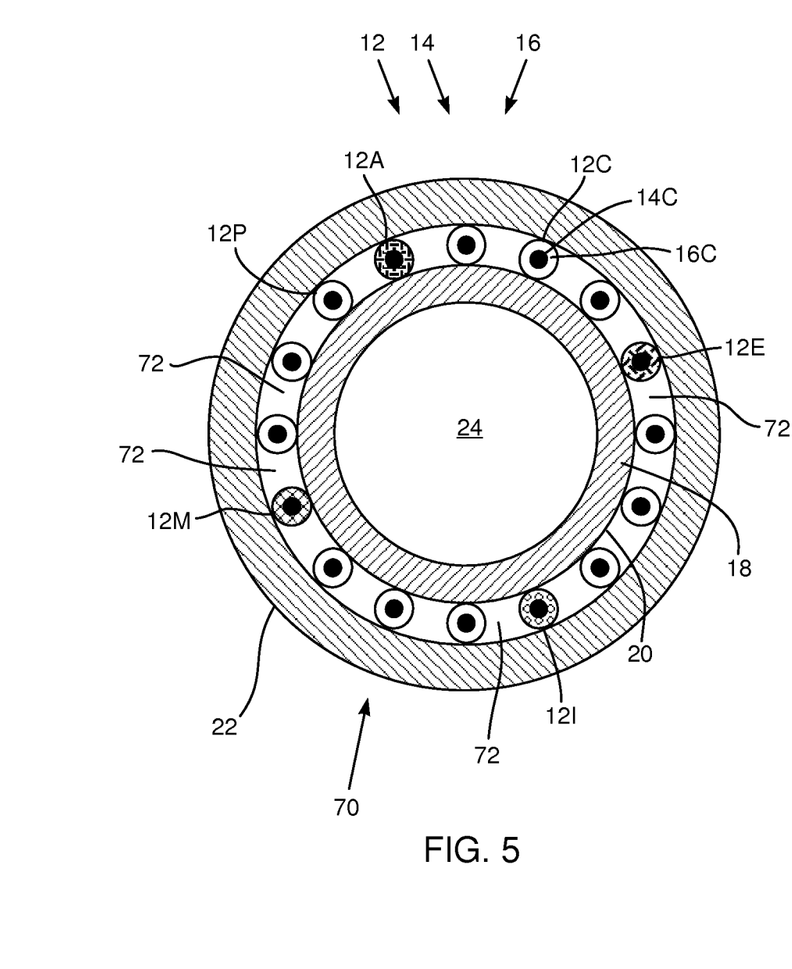
FIG. 5 is a schematic cross-sectional view of cabling, according to a yet further embodiment of the present invention.

FIG. 5 is a schematic cross-sectional view of cabling 70, according to an embodiment of the present invention. Apart from the differences described below, the structure of cabling 70 is generally similar to that of cabling 10 (FIGS. 1A and 1B), and elements indicated by the same reference numerals in both cabling 10 and 70 are generally similar in construction and in operation.

Cabling 70 has a similar multi-start thread configuration to that of cabling 10. The embodiment illustrated in FIG. 5 has 16 wires 12, so that in this example cabling 70, as for cabling 10, is topologically equivalent to a 16-start thread configuration.

However, in contrast to cabling 10, cabling 70 is configured to have equal spaces 72 between adjacent wires 12. During construction of cabling 70, material of sheath 22 typically fills in spaces 72, and bonds to core 18. In some embodiments, the separation between adjacent wires 12, due to spaces 72, is approximately equal to a diameter of the wires. In other embodiments the spacing generated by spaces 72 is smaller or larger than the diameter of wires 12. For the 16 wire embodiment illustrated in FIG. 5 there are 16 spaces 72 between the wires. In general for n wires 12, cabling 70 comprises n equal spaces 72.

The implementation of spacing between wires 12 in cabling 70 makes exposure of a specific wire 12 easier, by reducing the chance of inadvertently exposing a neighboring wire.

Figure 6:
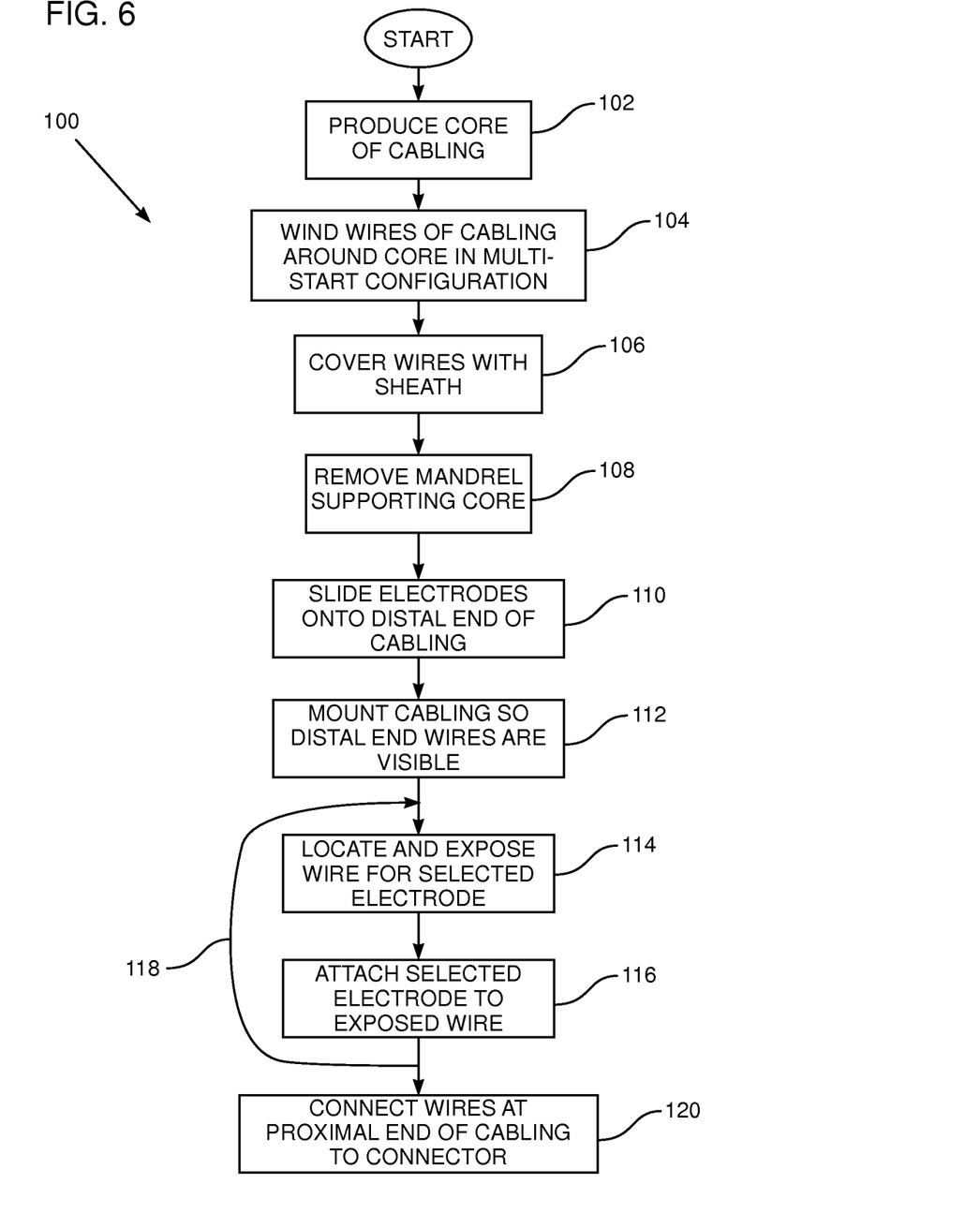
FIG. 6 is a flowchart describing steps in producing cabling, according to an embodiment of the present invention.

FIG. 6 is a flowchart 100, describing steps in producing cabling 10, according to an embodiment of the present invention. Those having ordinary skill in the art will be able to adapt the following description, mutatis mutandis, for the production of cabling 50, cabling 60, or cabling 70.

In an initial step 102, core 18 is produced. Typically, a core of 40D pebax such as that described above is formed by using a cylindrical copper wire as a mandrel. The mandrel is covered with a layer of PTFE (polytetrafluoroethylene), the PTFE is coated with a layer of 40D pebax, and the pebax layer is then allowed to harden to form a cylindrical tube.

In a coiling step 104 wires 12 are wound onto core 18 in the multi-start thread configuration described above with reference to FIGS. 1A and 1B. The inventors have found that it may be advantageous for core 18 to have mild adhesive properties, so as to maintain wires 12 in place after they have been coiled onto the core. Pebax has these type of adhesive properties. Wires 12 are typically configured so that they may be differentiated from each other, for instance by having one wire visually different from the others, and acting as a fiducial or index for all wires 12. Wire differentiation may be accomplished by coloring one or more of the insulating layers of the wires, as is described above with reference to FIGS. 1A and 1B.

In a cable covering step 106, protective sheath 22 is formed over wires 12. Typically the sheath is configured to be transparent. The sheath may be made from 55D pebax, without additives, that is formed over wires 12 in multiple layers that are allowed to harden separately.

In a mandrel removal step 108, the mandrel upon which the cabling has been formed is removed. Typically, the removal is accomplished by stretching the copper wire upon which core 18 is mounted. The stretching reduces the diameter of the mandrel, and the reduced mandrel diameter together with the presence of the PTFE covering the mandrel allows the mandrel to be slid from the cabling. Removal of the mandrel completes formation of cabling 10.

In a first electrode attachment step 110, ring electrodes 40 are slid onto a distal end of cabling 10. The number of electrodes that are slid onto the cabling depends on the number of different wires 12 in the cabling. Thus, for the embodiment described above having 16 different wires, up to 16 electrodes 40 may be connected to wires 12. In some embodiments less than the maximum number of electrodes may be used. For example, in the 16 wire embodiment described herein, 13 electrodes may be connected, and the remaining three wires may be used for conveying signals of components attached to the distal end, such as a force meter, a temperature gauge, and a location sensor.

In a mounting step 112, cabling 10, with electrodes 40 on the cabling, is mounted so that the wires of the distal end are visible, and so that the electrodes may be slid onto desired locations of the distal end. Typically, the cabling is mounted using chucks, such as are described in the above-referenced U.S. Patent Application 2012/0172714.

In a wire access step 114, a wire to which a selected electrode 40 is to be connected is located, typically using colored wires 12 as indexes. For example, assuming the four colored wire configuration described above, wire 12F may be identified as the first wire, in a proximal direction, measured from black wire 12E.

Once the wire has been located, the conductor of the wire is exposed by removing a section of sheath 22, and the corresponding section of the insulating layer of the wire to open a channel, such as channel 42 (FIG. 2A), to the conductor. The removal may be by any suitable means known in the art. The inventors have found that removal using a laser, or removal by careful mechanical cutting of the sheath and of the insulating layer, are both satisfactory.

In a second electrode attachment step 116, a selected electrode 40 is attached to the exposed conductor of the specific wire. For example, selected electrode 40 may be attached to conductor 16F of wire 12F. The attachment may be by feeding conductive cement into the opened channel, having the electrode contact the cement, then crimping the electrode, as described above with reference to FIG. 2B. Alternatively, the exposed conductor may be pulled out through the opened channel, and directly soldered or welded to the selected electrode.

As shown by an arrow 118, steps 114 and 116 are repeated for each electrode 40 that is to be attached to the distal end of cabling 10.

In a proximal end operation step 120, conductors of wires 12 of cabling 10 are exposed at the proximal end of cabling 10, and the exposed conductors are connected to a cabling connector. The actions performed in step 120 are generally similar in manner to those described for steps 114 and 116. For example, the first wire in the proximal direction measured from black wire 12E corresponds to wire 12F. A selected pin of the cabling connector may be connected to conductor 16F, after it has been exposed at the proximal end of the cabling, so that the selected pin connects to the electrode selected in step 116 above.

In a disclosed embodiment, a flexible printed circuit (PC) strip is attached to the connector, and pads along the PC strip are connected by traces to the connector. Typically the pads are arranged in a line along the strip, and respective pads may be connected to their wires, and thus to their respective electrodes, after the wires at the proximal end of cabling 10 have been exposed as described above.

Figure 7:
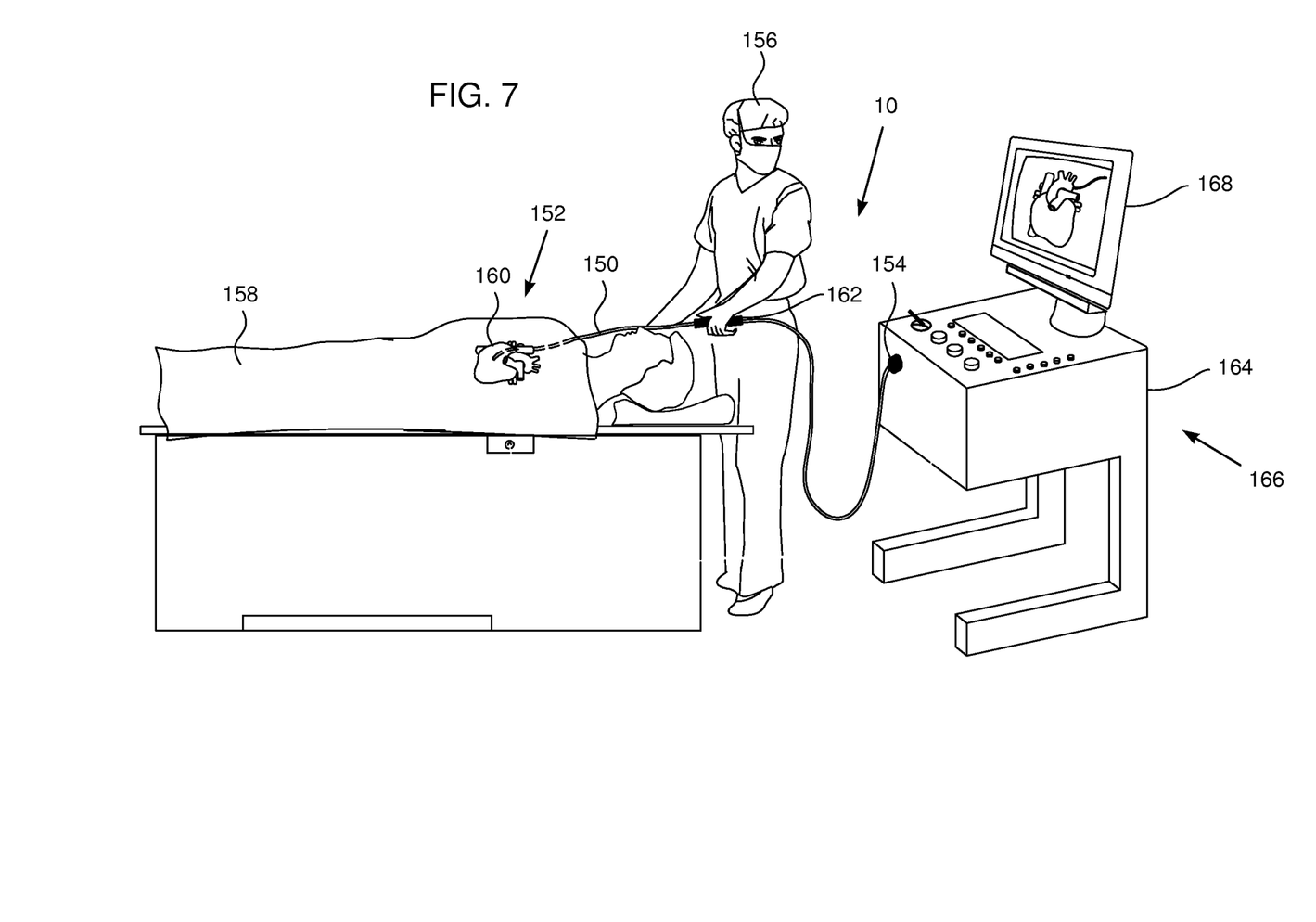
FIG. 7 is a schematic illustration of an invasive medical procedure using cabling, according to an embodiment of the present invention.

FIG. 7 is a schematic illustration of an invasive medical procedure using cabling 10, according to an embodiment of the present invention. The description for cabling 10 may be applied, mutatis mutandis, to a procedure using cabling 50 or cabling 60 or cabling 70. In preparation for the procedure, cabling 10 is incorporated into a catheter 150, the cabling having electrodes 152 at its distal end, and a connector 154 for the cabling at the proximal end of the cabling. Electrodes 152 are substantially similar to electrodes 40, and electrodes 152 and connector 154 are connected to cabling 10 substantially as described above in flowchart 100. Catheter 150 uses one set of cabling 10, and is typically any catheter which is not split at its distal end. For example, at its distal end catheter 150 may be straight or curved as a lasso or helical catheter.

By way of example, a medical professional 156 is assumed to insert catheter 150 into a patient 158 in order to acquire electropotential signals from heart 160 of the patient. The professional uses a handle 162 attached to the catheter in order to perform the insertion, and signals generated at electrodes 152 are conveyed via connector 154 to a console 164.

Console 164 comprises a processing unit 166 which analyzes the received signals, and which may present results of the analysis on a display 168 attached to the console. The results are typically in the form of a map, numerical displays, and/or graphs derived from the signals.

Figure 8:
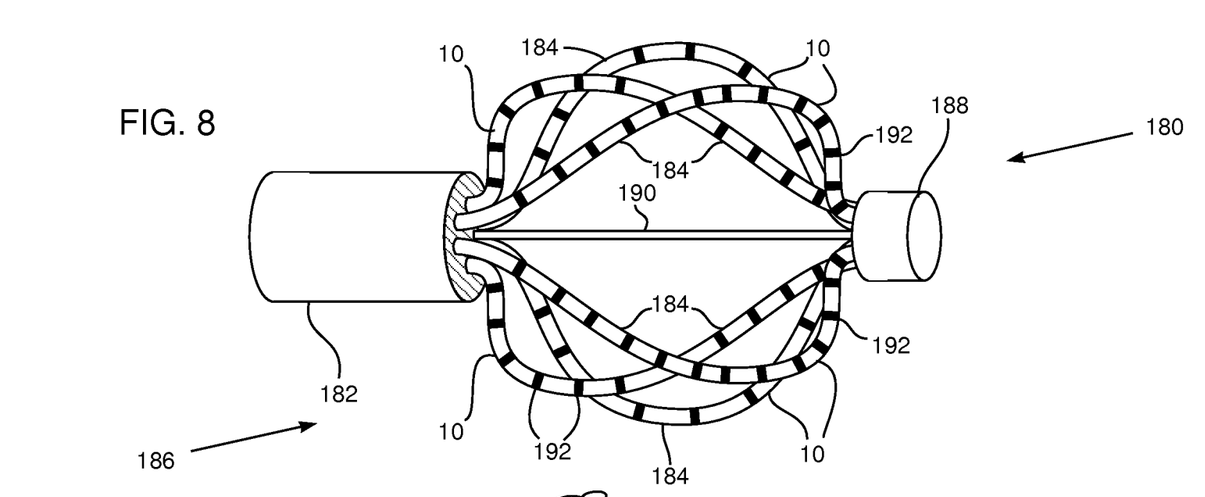
FIG. 8 is a schematic perspective view of a distal end of a basket catheter, according to an embodiment of the present invention.

FIG. 8 is a schematic perspective view of a distal end of a basket catheter 180, according to an embodiment of the present invention. Except as described below, basket catheter 180 is generally similar in construction and operation to catheter 150, described above. In contrast to catheter 150, basket catheter 180 uses a multiplicity of substantially similar cablings 10. Basket catheter 180 is generally similar in design to the basket catheter described in U.S. Pat. No. 6,748,255, to Fuimaono, et al., which is assigned to the assignees of the present invention, and which is incorporated herein by reference. In catheter 180, cablings 10 are incorporated into a solid cylindrical retaining cable 182, which acts to enclose cablings 10, and to hold the cablings rigidly in place with respect to each other within the cable. Typically, retaining cable 182 is formed of plastic.

In a disclosed embodiment the distal ends of cablings 10 of the basket catheter are formed as spines 184 of a basket assembly 186. Thus, as illustrated, spines 184 are connected together at their proximal ends by cable 182, and are connected together at their distal ends by a retaining plastic piece 188. Typically, basket catheter 180 comprises an expander 190 which may be used, as described in the above-referenced patent to Fuimaono, et al., to expand and contract assembly 186.

Each given spine 184 of assembly 186 has a set of electrodes 192 attached to the spine, the electrodes being substantially similar to electrodes 40, and being attached to their respective cablings 10 substantially as described above in flowchart 100. It will be understood that while the arrangements of the sets of electrodes in each spine may be the same, in some embodiments the arrangements of the electrodes in at least some of the spines may be different from the arrangement in other spines.

While basket catheter 180 is illustrated as having six spines 184, it will be understood that the basket catheter may have other numbers of cablings 10, the numbers being larger or smaller than six, incorporated into retaining cable 182. Each cabling 10 is used to form a corresponding spine 184.

Spines 184 may be approximately equal in length; alternatively the spines may be unequal in length. In one embodiment, spines 184 are unequal in length and are selected so that catheter 180 is approximately hemispherical, the spines forming ribs of a hemisphere.

Figure 9:
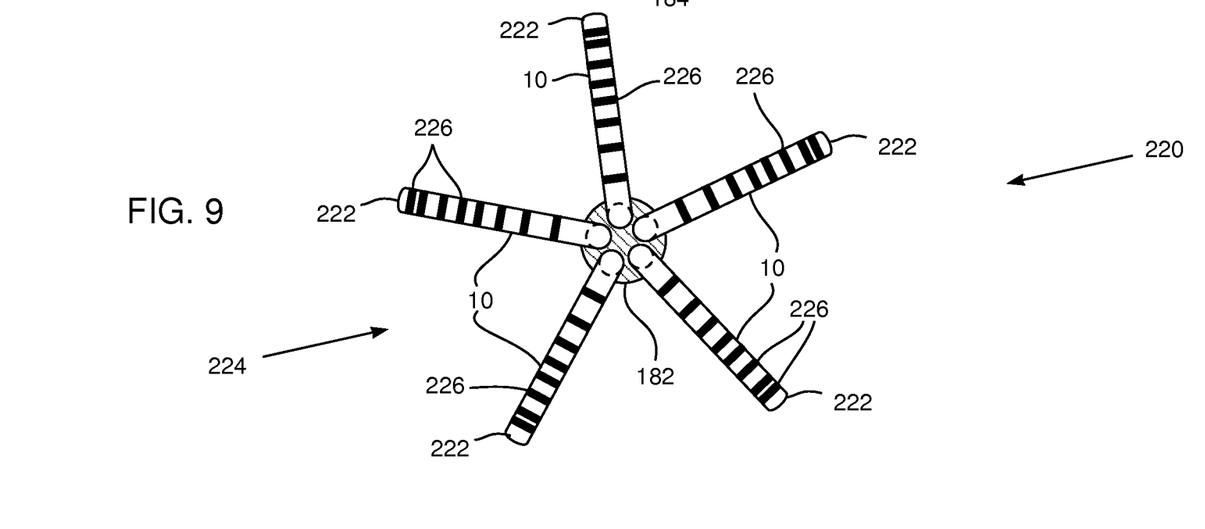
FIG. 9 is a schematic end view of a distal end of a catheter, according to an alternative embodiment of the present invention.

FIG. 9 is a schematic end view of a distal end of a catheter 220, according to an embodiment of the present invention. Except as described below, catheter 220 is generally similar in construction and operation to catheter 180, and elements indicated by the same reference numerals in both catheters 180 and 220 are generally similar in construction and in operation.

As for catheter 180, catheter 220 comprises a multiplicity of substantially similar cablings 10, which are incorporated into solid cylindrical retaining cable 182, which holds cablings 10 rigidly in place.

In contrast to catheter 180, in catheter 220 the distal ends of cablings 10 are not connected together at their distal ends. Rather, the distal ends of cablings 10 are formed as spokes 222 of a wheel in a star-shaped assembly 224 that forms a plane that is approximately orthogonal to cable 182. Thus, as illustrated, spokes 222 are connected together at their proximal ends by cable 182, but are unconnected at their distal ends. In some embodiments spokes 222 lie in a single plane, corresponding to the plane of the paper. However, in other embodiments at least some of spokes 222 are above or below the plane of the paper. A catheter generally similar in form to catheter 220 is the "Pentaray" catheter produced by Biosense Webster of Diamond Bar, Calif. In an alternative embodiment, spokes 220 form a plane that includes cable 182, so that the spokes appear in a "paint-brush" configuration.

Each spoke 222 of star-shaped assembly 224 has a set of electrodes 226 attached to the spine, the electrodes being substantially similar to electrodes 40 and being attached to their respective cablings 10 substantially as described above in flowchart 100. While the arrangements of the sets of electrodes in each spoke may be the same, in some embodiments the arrangements of the electrodes in at least some of the spokes may be different from the arrangement in other spokes.

Although catheter 220 is illustrated as having five spokes 222, it will be understood that the catheter may have other numbers of cablings 10, the numbers being larger or smaller than five, incorporated into retaining cable 182. Each cabling 10 is used to form a corresponding spoke 222.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Electrode cabling, comprising:
   a hollow core;
   n wires coiled on an outer surface of the core, the n wires having n respective conductors and n respective insulating layers, the n wires consisting of a single close-packed layer and in an arrangement topologically equivalent to an n-start thread configuration, each n respective insulating layer in the closed-packed layer being in continuous contact with at least one adjacent n respective insulating layer, wherein n is an integer greater than one;
   a sheath covering the n wires; and
   a ring electrode having a location along the sheath attached through a channel formed in the sheath at the location and a respective one of the n respective insulating layers to a given wire selected from the n wires.

2. The cabling according to claim 1, and comprising up to (n−1) further ring electrodes attached through the sheath to up to (n−1) respective wires other than the given wire.

3. The cabling according to claim 1, wherein at least one of the n wires is configured to act as an index wire for the n wires.

4. The cabling according to claim 3, wherein the index wire is visually different in appearance from the n wires not including the index wire.

5. The cabling according to claim 1, wherein the sheath is transparent.

6. The cabling according to claim 1, wherein the ring electrode is attached to the given wire at a distal end of the cabling, and comprising a connector attached at a proximal end of the cabling to the given wire.

7. The cabling according to claim 1, wherein the cabling is configured for use as a medical catheter.

8. The cabling according to claim 1, wherein the core is cylindrical, and wherein the n wires are coiled on the core in the n-start thread configuration.

9. A catheter, comprising:
   a retaining cable, comprising a plurality of electrode cablings, each electrode cabling comprising:
      a hollow core;
      n wires coiled on an outer surface of the core, the n wires having n respective conductors and n respective insulating layers, the n wires consisting of a single closed-packed layer and in an arrangement topologically equivalent to an n-start thread configuration, each n respective insulating layer in the closed-packed layer being in continuous contact with at least one adjacent n respective insulating layer, wherein n is an integer greater than one;
a sheath covering the n wires; and
up to n ring electrodes, each having a location along the sheath and each respectively attached through a channel formed in the sheath at its location and a respective one of the n respective insulating layers to up to n different wires of the arrangement.

10. The catheter according to claim 9, wherein distal ends of the plurality of electrode cablings are configured as spokes radiating from the retaining cable.

11. The catheter according to claim 10, wherein the spokes form a plane orthogonal to the retaining cable.

12. The catheter according to claim 10, wherein the spokes form a plane which includes the retaining cable.

13. The catheter according to claim 9, wherein distal ends of the plurality of electrode cablings are configured as spines of a basket assembly, wherein the spines are connected at the proximal ends thereof to the retaining cable, and the spines are connected to each other at the distal ends thereof.

14. The catheter according to claim 13, wherein the spines are equal in length.

15. The catheter according to claim 13, wherein the spines are unequal in length.

16. The catheter according to claim 15, wherein the spines form ribs of a hemisphere.

17. Cabling, comprising:
a hollow core;
n optical fibers coiled on an outer surface of the core, the n optical fibers consisting of a single closed-packed layer and in an arrangement topologically equivalent to an n-start thread configuration, an outer surface of a first n optical fiber in the closed-packed layer being in constant contact with the outside surface of at least one other n optical fiber, wherein n is an integer greater than one;
a sheath covering the n optical fibers; and
a sensor having a location along the sheath attached through a channel formed in the sheath at the location to a given optical fiber selected from the optical fibers.

18. Cabling, comprising: a hollow core; a plurality of active elements, the active elements comprising, n optical fibers coiled on the core, wherein n is an integer greater than zero; and m wires coiled on the core, wherein m is an integer greater than zero, and wherein the n optical fibers and the m wires consist of a single close-packed layer coiled on the hollow core and in an arrangement topologically equivalent to an (n+m)-start thread configuration, an outer surface of a first active element in the close packed layer being in contact with the outer surface of a second active element; and a sheath covering the n optical fibers and the m wires and having at least one channel formed therein.

19. A method for forming an electrode cabling comprising:
coiling n wires on an outer surface of a hollow core, the n wires having n respective conductors an n respective insulating layers, wherein the n wires consist of a single closed-packed layer and in an arrangement topologically equivalent to an n-start thread configuration, each n respective insulating layer in the closed-packed layer being in continuous contact with at least one adjacent n respective insulating layer, wherein n is an integer greater than one;
covering the n wires with a sheath; and
attaching a ring electrode having a location along the sheath through a channel formed in the sheath at the location and a respective one of the n respective insulating layers to a given wire in the arrangement.

20. The method according to claim 19, and comprising attaching up to (n−1) further ring electrodes through the sheath to up to (n−1) respective wires other than the given wire.

21. The method according to claim 19, and comprising configuring at least one of the n wires to act as an index wire for the n wires.

22. The method according to claim 21, wherein the index wire is visually different in appearance from the n wires not including the index wire.

23. The method according to claim 19, wherein the sheath is transparent.

24. The method according to claim 19, and comprising attaching the ring electrode to the given wire at a distal end of the electrode cabling, and attaching a connector at a proximal end of the electrode cabling to the given wire.

25. The method according to claim 19, and comprising configuring the electrode cabling for use as a medical catheter.

26. The method according to claim 19, wherein the core is cylindrical, the method comprising coiling the n wires on the core in the n-start thread configuration.

27. The method according to claim 19, wherein the core encloses a shape memory element.

28. A method for producing a catheter, comprising:
enclosing a plurality of electrode cablings within a retaining cable; and
for each electrode cabling:
coiling n wires on an outer surface of a hollow core, the n wires having n respective conductors and n respective insulating layers, the n wires consisting of a single closed-packed layer and in an arrangement topologically equivalent to an n-start thread configuration, each n respective insulating layer in the closed-packed layer being in continuous contact with at least one adjacent n respective insulating layer, wherein n is an integer greater than one;
covering the n wires with a sheath; and
respectively attaching up to n ring electrodes, each having a location along the sheath each through a channel formed in the sheath at its location and a respective one of the n respective insulating layers to up to n different wires in the arrangement.

29. The method according to claim 28, and comprising configuring distal ends of the plurality of electrode cablings as spokes radiating from the retaining cable.

30. The method according to claim 29, wherein the spokes form a plane orthogonal to the retaining cable.

31. The method according to claim 29, wherein the spokes form a plane which includes the retaining cable.

32. The method according to claim 28, and comprising configuring distal ends of the plurality of electrode cablings as spines of a basket assembly wherein the spines are connected at the proximal ends thereof to the retaining cable and are connected to each other at the distal ends thereof.

33. The method according to claim 32, wherein the spines are equal in length.

34. The method according to claim 32, wherein the spines are unequal in length.

35. The method according to claim 34, wherein the spines form ribs of a hemisphere.

36. A method, comprising: coiling n optical fibers on an outer surface of a hollow core, the n optical fibers consisting of a single closed-packed layer and in an arrangement topologically equivalent to an n-start thread configuration, an outer surface of a first n optical fiber in the closed-packed layer being in constant contact with the outside surface of at least one other n optical fiber, wherein n is an integer greater than one; covering the n optical fibers with a sheath; and attaching a sensor having a location along the sheath through a channel formed in the sheath at the location to a given optical fiber selected from the optical fibers.

37. A method, comprising: providing a plurality of active elements, the active elements having a plurality of optical fibers and a plurality of wires; coiling n optical fibers on a hollow core, wherein n is an integer greater than zero; coiling m wires coiled on the core, wherein m is an integer greater than zero, and wherein the n optical fibers and the m wires consist of a single closed-packed layer coiled on the hollow core and in an arrangement topologically equivalent to an (n+m)-start thread configuration, an outer surface of a first active element in the close packed layer being in contact with the outer surface of a second active element; covering the n optical fibers and the m wires with a sheath; and attaching a sensor having a location along the sheath through a channel formed in the sheath at the location to a given optical fiber selected from the optical fibers.

* * * * *